United States Patent
Yellepeddi et al.

(10) Patent No.: US 9,031,187 B2
(45) Date of Patent: May 12, 2015

(54) METHOD AND APPARATUS FOR PERFORMING X-RAY ANALYSIS OF A SAMPLE

(75) Inventors: Ravisekhar Yellepeddi, Ecublens (CH); Pierre-Yves Negro, Ecublens (CH)

(73) Assignee: Thermo Fisher Scientific (Ecublens) SARL, Ecublens (CH)

( * ) Notice: Subject to any disclaimer, the term of this patent is extended or adjusted under 35 U.S.C. 154(b) by 305 days.

(21) Appl. No.: 13/515,939

(22) PCT Filed: Dec. 13, 2010

(86) PCT No.: PCT/EP2010/069540
§ 371 (c)(1),
(2), (4) Date: Jun. 14, 2012

(87) PCT Pub. No.: WO2011/073148
PCT Pub. Date: Jun. 23, 2011

(65) Prior Publication Data
US 2012/0294418 A1    Nov. 22, 2012

(30) Foreign Application Priority Data

Dec. 17, 2009    (GB) .................................. 0921965.0

(51) Int. Cl.
*G01N 23/223* (2006.01)
*G01N 23/207* (2006.01)

(52) U.S. Cl.
CPC ............ *G01N 23/223* (2013.01); *G01N 23/207* (2013.01); *G01N 2223/071* (2013.01); *G01N 2223/1016* (2013.01); *G01N 2223/076* (2013.01)

(58) Field of Classification Search
CPC ................ G01N 23/223; G01N 23/20; G01N 23/20008; G01N 23/20016; G01N 23/20025; G01N 23/20091; G01N 23/207; G01N 23/2076; G01N 2223/076; G01N 23/2204; G01N 23/2206; G01N 23/2208; G01N 23/203; G01N 23/205; G21K 1/06
USPC .............................. 378/44–46, 70–72, 79, 81
See application file for complete search history.

(56) References Cited

U.S. PATENT DOCUMENTS

| 3,344,274 A | 9/1967 | Ashby et al. |
| 4,263,510 A | 4/1981 | Ciccarelli et al. |

(Continued)

FOREIGN PATENT DOCUMENTS

| EP | 183043 B1 | 9/1989 |
| JP | 04184155 | 7/1992 |

(Continued)

*Primary Examiner* — Jurie Yun
(74) *Attorney, Agent, or Firm* — Gordon Stewart

(57) ABSTRACT

The invention provides an apparatus and a method of performing X-ray diffraction (XRD) and/or X-ray fluorescence (XRF) analysis of a sample, comprising: irradiating a sample with X-rays from an X-ray source; providing a combined XRD and XRF detection arrangement comprising a scanning wavelength selector and at least one X-ray detector for detecting X-rays selected by the wavelength selector; and performing XRD analysis of the sample by selecting at least one fixed wavelength of X-rays diffracted by the sample using the scanning wavelength selector and detecting X-rays of the selected fixed wavelength(s) at one or more values of the diffraction angle φ at the sample using the X-ray detector(s); and/or performing XRF analysis of the sample by scanning wavelengths of X-rays emitted by the sample using the scanning wavelength selector and detecting X-rays of the scanned wavelengths using the X-ray detector(s).

20 Claims, 12 Drawing Sheets

(56) References Cited

U.S. PATENT DOCUMENTS

| | | | |
|---|---|---|---|
| 4,916,720 A * | 4/1990 | Yamamoto et al. | 378/81 |
| 5,406,608 A | 4/1995 | Yellepeddi et al. | |
| 6,798,863 B2 | 9/2004 | Sato | |
| 2006/0088139 A1 | 4/2006 | Nakano et al. | |

FOREIGN PATENT DOCUMENTS

| | | |
|---|---|---|
| JP | 09257726 | 10/1997 |
| JP | 09318565 | 12/1997 |
| JP | 2011502312 | 2/1999 |
| JP | 2003098126 | 4/2003 |
| JP | 2006213836 | 8/2006 |
| WO | 9713142 A1 | 4/1997 |
| WO | 9725614 A1 | 7/1997 |
| WO | 2008107108 A1 | 9/2008 |

* cited by examiner

METHOD AND APPARATUS FOR PERFORMING X-RAY ANALYSIS OF A SAMPLE

FIELD

The present invention relates to a method and apparatus for performing X-ray analysis of a sample, in particular for performing both X-ray diffraction and X-ray fluorescence analysis of the sample.

BACKGROUND

Analysis of samples by using X-rays is well known. The technique of X-ray diffraction (XRD) is used to determine the structural (i.e. crystallographic) properties of a crystalline sample. In XRD, the X-Ray diffractometer usually incorporates a monochromatic X-Ray source, which is typically collimated or focused for irradiating a sample to be analysed and which has an intense characteristic X-ray line, e.g. at 8.043 keV, and a detector which is optimized to detect this radiation after it has been diffracted by the sample. Typically, both the X-ray source and the detector are angularly moved (rotated) around the sample in order to scan the diffraction angle ($\phi$), which angle is shown in FIG. 1. There are many variants of diffraction setups optimized for specific applications. Usually the sample to be analyzed is polycrystalline which means that crystallites of small size are isotropically and randomly distributed in the sample. Depending on their direction, the incident X-rays can reach an ensemble of crystallites which are distributed with a crystal plane oriented in such a way that collective diffraction from these crystallites occurs for a given direction of detection, i.e. along a given diffraction angle ($\phi$) as determined by Bragg's law. There are also issues regarding incident and diffracted beam attenuation along the path length inside the sample which can be mitigated by favoring diffraction from crystallites which are in the vicinity of the surface of the sample. This can be done by tilting the sample. Detection of the diffracted X-rays over a range of angles provides an angular diffraction pattern or diffractogram having characteristic peaks of diffracted intensity when the condition of Bragg's law is satisfied and information on the crystalline structure of the analyzed sample can be obtained from this angular diffraction pattern. However, XRD does not provide information about the elemental composition of the sample.

In order to obtain information on the elemental composition of a sample, different techniques can be used, such as chemical (e.g. titration) or spectroscopic (e.g. optical emission), all having their own advantages and drawbacks. The X-ray fluorescence (XRF) phenomenon can be used to perform elemental analysis and to obtain accurate, quantitative composition information on a sample non-destructively. In the XRF technique, a sample is irradiated with an X-Ray beam which induces the emission of secondary X-rays having wavelengths characteristic of the constituents elements of the material. In order to induce X-Ray fluorescence on the broadest variety of materials, a polychromatic X-Ray source is used to access the widest possible range of wavelengths. XRF spectrometers are of the Energy Dispersive (EDXRF) or wavelength dispersive (WDXRF) type. The principal features of a WDXRF apparatus are: a polychromatic, usually divergent X-Ray source, a dispersing means to select the wavelength peaks of interest and an X-ray detector. The dispersing means is usually a flat or curved crystal, having respectively parallel or focusing beam optics. Changing the angle ($\theta$) between the crystal and the detector allows scanning of the wavelength of the emitted secondary X-rays reaching the detector. State of the art XRF apparatus may incorporate several static or simultaneous detection channels each with its own crystal and associated fixed wavelength which detect simultaneously and/or a rotating device to sequentially scan the wavelengths of interest. However, the XRF technique does not provide information about the structure or crystalline phases of the sample.

In view of the above discussion it can be seen that it would be desirable to provide both XRD and XRF techniques in a single instrument to increase analysis capabilities, as well as to reduce both cost and footprint in the laboratory. However, this is complicated because the requirements of the two techniques are very different as described above.

There are several prior art apparatus for performing XRF and XRD with the same instrument. Some prior art solutions have employed two X-ray sources, e.g. as described in U.S. Pat. No. 3,344,274 and WO 2008/107108 A1. Such designs are clearly complex and expensive. Another prior art design is described in EP 183,043, which uses a single X-ray source but requires a complex arrangement of goniometers in order to produce an apparatus capable of both XRF and XRD. The latter design can result in difficulties due to the precision and reproducibility necessary when the geometry of the device is changed.

Another prior art solution is described in U.S. Pat. No. 5,406,608 which uses a single vertically mounted X-ray source and implements multiple XRF channels mounted azimuthally around the X-ray tube. The XRF channels can only be used for XRF measurements. In addition to the XRF channels, there is a separate XRD monochromatic detection arrangement rotating around the sample. The XRD detection arrangement comprises a collimator, a crystal and a detector. This arrangement is mounted on a support which can be moved around the sample by means of an actuator to record the XRD pattern. This detection arrangement is dedicated to XRD measurement and the angle between detector and crystal is fixed so as to be optimised for XRD. However, this design suffers the drawback that the XRD detection is separate from the XRF detection, which requires additional space and multiple components.

In WO 97/25614, an apparatus with two separate detection systems has been proposed (one scanning WDXRF system optimized for XRF, and a fixed monochromatic system for XRD), at the expense of increased cost, size and complexity. In that case it is noted moreover that the diffraction angle is scanned using only primary collimator tilt, i.e. no goniometer, which allows only scanning a very limited portion of the diffraction spectrum. Another apparatus with two separate detection systems has been proposed in WO 97/13142.

There are also known prior art designs with one or a plurality of monochromatic XRD sources used to illuminate the sample for XRD and XRF measurement, e.g. as described in US 2006/088139A1 or U.S. Pat. No. 6,798,863. However, the instruments cannot perform effective state of the art X-Ray fluorescence measurements because they use a specific XRD radiation source which strongly limits the range of compositions that can be measured by fluorescence. In addition, in these cases the XRF detector is of an energy dispersive (EDX) type and XRF performances are accordingly limited as compared to using a wavelength dispersive type. Moreover, in U.S. Pat. No. 6,798,863 the XRD pattern is recorded using a CCD line or strip detector which again limits performance and requires a specific additional component only used for XRD application. Whilst a strip detector allows simultaneous acquisition of the diffraction pattern, numerous drawbacks include not being usable with parallel (collimating) geometry, potential spectral distortion, insufficient energy discrimination, complex data acquisition electronics and not being usable for peak follow-up, as well as usually being of higher cost.

A common detection arrangement performing for both XRF and XRD is not trivial to achieve, since it requires compromises, e.g. regarding the choice of X-ray source, crystal types and of collimator divergence. Also, detecting wavelengths for XRD using detectors commonly used in XRF is unusual since the energy spectrum of the X-Rays is quite different for XRD and XRF. In U.S. Pat. No. 4,263,510 is disclosed an XRD-XRF apparatus, which is again primarily optimized for XRD as is indicated by its point-like source collimator optimised for the type of anode geometry commonly used in X-ray tubes used for XRD (monochromatic X-ray tubes). The X-ray tube is also positioned relatively far from the sample which results in reduced X-ray fluorescence signals, since XRF apparatus should illuminate an area as large as possible on the sample surface with a polychromatic X-Ray source located as close as possible to the sample to get maximum fluorescence intensity. For the X-ray detector, U.S. Pat. No. 4,263,510 refers to the use of an energy dispersive (EDX) or wave-dispersive (WDX) analyser, although the drawings therein strongly imply the need for energy dispersive detection due to the compact nature of the detector illustrated. Moreover, due to the position of the XRD X-ray tube far from the sample, and due to it appearing to be a monochromatic tube, the detector would be required to be of the energy dispersive type for the apparatus to have any practical use as an XRF apparatus, since the X-ray signal would be too low for effective detection by wave-dispersive analysis and certainly not wavelength dispersive analysis using a wavelength scanning device (monochromator) rather than a polychromator. This limits severely the extent and flexibility of XRF measurements which can be made using the apparatus. Thus, in order to record XRF with good sensitivity as well as XRD it has generally been required to use two separate detection systems for XRF and XRD as discussed above.

In view of the above background the present invention has been made.

SUMMARY

According to an aspect of the present invention there is provided a method of performing X-ray diffraction (XRD) and/or X-ray fluorescence (XRF) analysis of a sample, comprising:

irradiating a sample with X-rays from an X-ray source;

providing a combined XRD and XRF detection arrangement comprising a scanning wavelength selector and at least one X-ray detector for detecting X-rays selected by the wavelength selector; and performing XRD analysis of the sample by selecting at least one fixed wavelength of X-rays diffracted by the sample using the scanning wavelength selector and detecting X-rays of the selected fixed wavelength(s) at one or more values of the diffraction angle $\phi$ at the sample using the at least one X-ray detector; and/or performing XRF analysis of the sample by scanning wavelengths of X-rays emitted by the sample using the scanning wavelength selector and detecting X-rays of the scanned wavelengths using the at least one X-ray detector.

According to another aspect of the present invention there is provided an apparatus for performing X-ray diffraction (XRD) and X-ray fluorescence (XRF) analysis of a sample, comprising:

an X-ray source;

a sample holder for holding a sample so that it may be irradiated by X-rays from the X-ray source; and a combined XRD and XRF detection arrangement comprising a scanning wavelength selector and at least one X-ray detector for detecting X-rays selected by the wavelength selector;

wherein the apparatus is operable to perform:

(i) XRD analysis of the sample by selecting at least one fixed wavelength of X-rays diffracted by the sample using the scanning wavelength selector and detecting X-rays of the selected wavelength(s) at one or more values of the diffraction angle $\phi$ at the sample using the at least one X-ray detector; and (ii) XRF analysis of the sample by scanning wavelengths of X-rays emitted by the sample using the wavelength selector and detecting X-rays of the scanned wavelengths using the X-ray detector.

The present invention enables use of the same components (i.e. the components of the combined XRD and XRF detection arrangement) to act as both a diffractometer for XRD analysis and a spectrometer for XRF analysis. In other words, the combined XRD and XRF detection arrangement is capable of detecting X-rays for both XRD and XRF measurements of the sample. Advantageously, the invention involves no complexity in switching over from one technique to the other. By using a single combined detection arrangement, which can be used either for wavelength dispersive XRF (WDXRF) measurement by scanning the wavelength of the received X-ray fluorescence emission or for XRD analysis by selecting and fixing an appropriate wavelength or wavelengths and scanning the diffraction angle at the sample, embodiments of the invention make a substantial saving in both cost and space of components in the apparatus. The apparatus may therefore be made cheaper and smaller than existing designs which combine XRD and XRF measurement in one instrument, leading to a smaller footprint in the laboratory or field. Moreover, the present invention may be implemented with a single X-ray source again being advantageous for cost and space reasons. The invention, in simple embodiments, may be implemented using only one wavelength selector and only X-ray detector for use in both XRD and XRF analysis, thus providing a compact and inexpensive combined XRD/XRF instrument.

Preferably, the X-rays are polychromatic, i.e. the X-ray source is preferably a polychromatic X-ray source. In combination with the scanning wavelength selector this provides for an apparatus and method optimised for XRF on a wide range of samples as well as being capable of performing XRD, both using the same detection arrangement.

Preferably, the invention comprises providing a first or primary collimating element between the X-ray source and the sample so that the sample is irradiated with a parallel X-ray beam.

Preferably, the X-ray source is mounted at an angle of less than 90 degrees to the sample.

For recording an XRD pattern (i.e. a pattern of diffracted X-ray intensity against diffraction angle), the diffraction angle at the sample, $\phi$, is varied and the X-rays of selected wavelength are detected at a plurality of values of $\phi$. Variation of $\phi$ may also be desirable to align the combined detector arrangement on the center of a diffraction peak, e.g. where detection of a single diffraction peak is required. Accordingly, for XRD the method of the invention preferably comprises varying the diffraction angle $\phi$ at the sample of the selected fixed wavelength(s) of X-rays, i.e. detecting X-rays of the selected fixed wavelength(s) at a plurality of values of the diffraction angle φ at the sample. The apparatus is therefore preferably operable to perform XRD analysis of the sample by selecting at least one fixed wavelength of X-rays diffracted by the sample using the wavelength selector, varying the diffraction angle φ at the sample of the selected wavelength(s) of X-rays and detecting X-rays of the selected wavelength(s). An angular scanning means is therefore preferably provided for varying the diffraction angle φ at the sample of the X-rays to be selected by the scanning wavelength selector. The angular scanning means, preferably comprises one of the following: means for moving the combined detector arrangement and/or the X-ray source; means for moving (e.g. tilting) a primary collimator positioned between the X-ray source and the sample. The angular scanning means more preferably comprises a goniometer. As used herein, the term goniometer is intended to mean any mechanism which allows a component mounted thereon to be rotated to a precise angular position as known in the art. For example, a goniometer may be provided for moving the combined detector arrangement and/or the X-ray source to precisely vary the diffraction angle of the X-rays at the sample. In embodiments, therefore, preferably one or both of the X-ray source and the combined XRD and XRF detection arrangement are mounted on a goniometer for varying the diffraction angle φ at the sample of the X-rays to be selected by the scanning wavelength selector and such a goniometer may be termed herein the primary goniometer. The combined XRD and XRF detection arrangement preferably also comprises at least one goniometer for varying the angle θ of the X-rays at a wavelength dispersive element (e.g. crystal) and such a goniometer may be termed herein a secondary goniometer. The secondary goniometer(s) is thus preferably mounted on the primary goniometer. In particular, the X-ray detector(s) may be mounted on a secondary goniometer. In some embodiments, e.g. for small variation of angle φ, the apparatus preferably further comprises a primary collimator to collimate X-rays from the source wherein the primary collimator is rotatably mounted (i.e. tiltable) for varying the diffraction angle φ at the sample of the X-rays to be selected by the scanning wavelength selector.

Preferably, varying the diffraction angle φ at the sample of the selected fixed wavelength(s) of X-rays comprises one or more of the following:

angularly moving the combined XRD and XRF detection arrangement about the sample;

angularly moving the X-ray source about the sample; and/or tilting the first collimating element relative to the sample.

In other words, the apparatus preferably comprises one or more of the following for varying the diffraction angle φ at the sample:

the combined XRD and XRF detection arrangement is angularly moveable about the sample;

the X-ray source is angularly moveable about the sample; and/or the first collimating element can be tilted relative to the sample.

In some embodiments, tilting the sample may permit access to different planes of polycrystallites. Thus, in such embodiments, the sample holder is preferably operable to tilt the sample.

Preferably, the invention comprises selecting one or more characteristic emission lines of the X-ray source as the fixed wavelengths in the XRD analysis by fixing a diffraction angle θ at the scanning wavelength selector, e.g. at a wavelength dispersive element of the wavelength selector.

In some preferred embodiments, the invention comprises in the XRD analysis selecting two or more fixed wavelengths and detecting the two or more fixed wavelengths X-rays using two or more X-ray detectors. Thus, in some preferred embodiments, the apparatus may comprise two or more X-ray detectors for detecting X-rays at different wavelengths. The two or more detectors preferably detect the X-rays sequentially.

Preferably, the invention comprises in the XRF analysis scanning wavelengths of X-rays emitted by the sample by scanning a diffraction angle θ at a wavelength dispersive element of the wavelength selector while the diffraction angle φ at the sample is fixed (kept constant). In preferred embodiments, the or each X-ray detector is mounted on a goniometer for varying the diffraction angle θ at the wavelength dispersive element of detected X-rays. Each detector may be mounted on a separate goniometer for varying the diffraction angle θ.

Preferably, the scanning wavelength selector comprises an entry collimating element, a wavelength dispersive element and at least one exit collimating element, the entry and exit collimating elements being positioned either side of the wavelength dispersive element, the at least one X-ray detector being positioned after the at least one exit collimating element, and the entry and exit collimating elements being positioned at an angle θ to the wavelength dispersive element wherein the angle θ can be varied to select or scan wavelengths of X-rays.

Preferably, the entry and exit collimating elements are each a collimator and the wavelength dispersive element is a flat crystal.

The XRD analysis may be performed by selecting one or more than one fixed wavelength of X-rays diffracted by the sample. Accordingly, the feature of selecting a fixed wavelength of X-rays diffracted by the sample herein means selecting at least one fixed wavelength of X-rays. A selected wavelength for XRD is referred to herein as a fixed wavelength since it is a wavelength which is selected for detection during the XRD analysis and is not varied during the XRD analysis. The selected fixed wavelength(s) is/are preferably selected to be the characteristic emission line(s) of the X-ray source/tube. In certain embodiments, which may be advantageous from the viewpoint of simplicity and cost, one fixed wavelength of X-rays diffracted by the sample is selected using the scanning wavelength selector for detection. In such embodiments only one X-ray detector may be needed to detect the selected wavelength of X-rays and one resultant XRD pattern (e.g. intensity versus diffraction angle) is obtained. In some other embodiments, which may be advantageous from the viewpoint of accuracy, two or more fixed wavelengths of X-rays diffracted by the sample are selected using the scanning wavelength selector for detection. In such embodiments the scanning wavelength selector may disperse the wavelengths of the diffracted X-rays and send each of the selected fixed wavelengths to a separate detector. Where two or more fixed wavelengths of X-rays diffracted by the sample are selected and detected simultaneously, two or more resultant XRD patterns may be obtained likewise simultaneously.

At least one X-ray detector is provided in the XRD and XRF detection arrangement. One X-ray detector may be provided for reasons of cost and simplicity. However, two or more X-ray detectors may be provided each for simultaneously or, more preferably, sequentially detecting a different wavelength range of X-rays, i.e. monochromated X-rays, from the sample in order to simultaneously or sequentially record more than one XRD pattern (when in XRD mode) and/or acquire an XRF spectrum more quickly or access a wider wavelength range or improve sensitivity since each detector may detect a different range of the wavelengths as they are scanned by the wavelength selector (when in XRF mode). Each detector may have optimum sensitivity for a specific X-ray wavelength range in order to improve performance. For example, for the lower energy ranges of the spectrum preferably gas detectors such as flow proportional counters (FPC) or sealed detectors are used and for higher energy ranges of the spectrum other detectors like scintillators are preferred.

Further variations of the invention include the use of multiple (i.e. more than one) wavelength dispersive elements in the combined XRD and XRF detection arrangement, e.g. multiple crystals, to extend the wavelength range for XRF or to improve the XRD measurement. In some embodiments, therefore, a plurality of crystals may be provided which can be interchanged in the detection arrangement, e.g. by automated interchanging means (for instance a rotating turret).

In order to extend the XRD measurements or improve the XRF capabilities, the X-ray source may be provided with a plurality of characteristic emission lines, e.g. by providing the X-ray tube with a plurality of anode materials.

DETAILED DESCRIPTION OF EMBODIMENTS OF THE INVENTION

Embodiments of the invention will now be described in more detail by way of example only with reference to the accompanying drawings in which.

Figure 1:
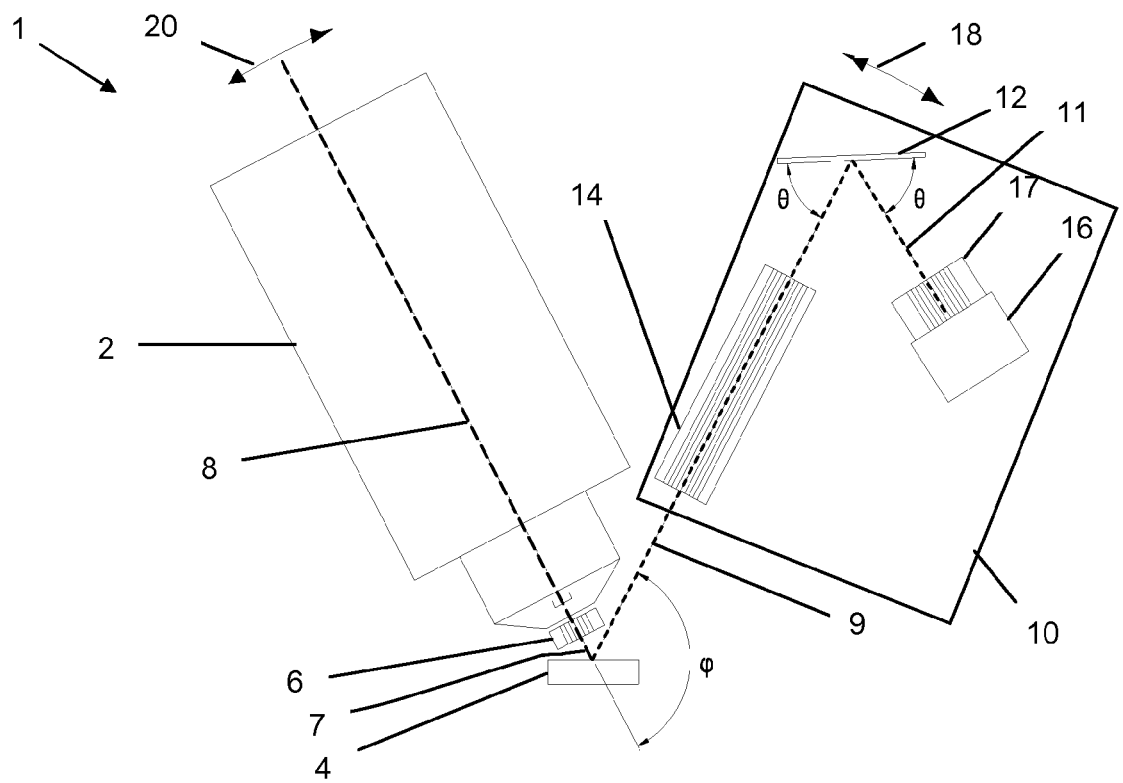
FIG. 1 shows schematically a side view of an embodiment of an apparatus according to the present invention.

Referring to FIG. 1 there is shown schematically an embodiment of an apparatus 1 according to the present invention. The apparatus 1 is typically (although not necessarily) housed inside a chamber (not shown) which can be evacuated and/or flushed with an appropriate gas in order to control the atmospheric environment as is known in the art of XRD and XRF. The apparatus 1 comprises an X-ray source 2 for irradiating a sample 4 which is held on a sample holder (not shown). The X-rays from the source 2 are in the form of an irradiating beam 7 which travels along a beam irradiation axis 8 to the sample 4. The irradiation axis is typically substantially co-axial with the long axis of the X-ray source.

The X-ray source of the present invention is preferably a polychromatic X-ray source, more preferably a polychromatic X-ray tube. The polychromatic X-ray tube is desirably of a type typically employed for XRF measurements. The present invention preferably employs a single X-ray source, e.g. a single X-ray tube, with which both the XRD and XRF may be carried out leading to significant cost savings. Suitable X-ray sources therefore may comprise one of the following types of X-ray tube: end-window X-ray tube, side-window X-ray tube, dual anode X-ray tube and transmission anode X-ray tube. A typical anode material for the X-ray tube is Rh but for specific applications other anode materials may be used including one or more of the following materials: Pd, Cr, Mo, W, Sc, Cu, Au or Pt. The X-ray source is preferably positioned in close proximity to the sample surface, e.g. as close as possible whilst allowing for a primary collimator to be positioned between the X-ray source and sample.

The X-rays from the source, at least for the XRD measurement, are preferably in the form of a parallel beam of X-rays. Accordingly, most preferably, the X-ray source is a polychromatic, parallel beam X-ray source. The sample is thus preferably irradiated with a parallel beam of X-rays from the source. Conveniently, the X-rays may be obtained as a parallel beam by passing the X-rays from an X-ray tube through a first, primary or source collimating element, preferably a collimator, herein termed a first, primary or source collimator. Preferred collimators for use in the present invention are Soller collimators. The sample is thus preferably irradiated with an X-Ray source through a primary Soller collimator. More than one collimating element (e.g. more than one collimator) may be provided which can be interchangeably positioned in the X-ray beam so as to vary the collimating of the beam on the sample. In the Figures, a primary collimator 6 is shown in front of the X-ray source 2. In some embodiments the primary collimator 6 is retractable so it may be moved laterally in and out of the X-ray beam as desired, e.g. moved out of the beam if only XRF is to be performed and moved into the beam if XRD is to be performed. With reference to FIG. 1, the primary collimator may be moved laterally in and out of the X-ray beam either in the plane of the page or perpendicular to the page. The primary collimator may be so moved by means of a driver (not shown), e.g. a linear driver. Accordingly, the invention may comprise a driver for moving the lateral position of the primary collimator. In some embodiments, described in more detail below, the primary collimator 6 may be tilted with respect to the x-ray beam which enters it so as to vary the angle of the beam irradiation axis which strikes the sample (and hence vary angle $\phi$ as described below). The primary collimator may be tilted by means of a driver, e.g. the same or different driver which may move the lateral position of the primary collimator. The driver for tilting the collimator may be a rotational driver. In FIG. 1, an XRF tube is used as the source 2 which emits polychromatic radiation, optimized for fluorescence, and provides via the collimator 6 a parallel beam incident on the sample.

The X-ray source may be mounted at any suitable angle to the sample (i.e. to provide the irradiation axis at any suitable angle). As will be described in more detail below, in some embodiments the X-ray source (and hence irradiation axis) may be angularly moveable (e.g. rotatable) about the sample whereas in other embodiments it may be fixed in position. The X-ray source may be mounted normally (i.e. orthogonally) to the sample (i.e. with the X-ray beam axis 8 normal to the sample surface and optionally substantially co-axial with the sample) or may be mounted at an angle of less than 90 degrees to the sample, herein termed at an angle (i.e. with the X-ray beam axis 8 at less than 90 degrees to the sample surface). Preferably, the X-ray source (and thereby irradiation axis 8) is mounted at an angle to the sample. This is in contrast to the prior art design described in U.S. Pat. No. 5,406,608 wherein the X-ray tube is mounted normally to the sample due to the need to accommodate XRF channels azimuthally around the tube as well as accommodate a separate XRD detection channel on one side. Mounting of the X-ray tube normally limits the range of diffraction angles which can be scanned and so the present invention preferably has the X-ray source mounted at an angle less than 90 degrees to the sample surface to advantageously allow a wider range of diffraction angles to be scanned as described in more detail below. Preferably, the X-ray source is mounted at an angle between 10 and 90 degrees to the sample surface, more preferably between 15 and 85 degrees, still more preferably between 60 and 80 degrees. In embodiments wherein the X-ray source is angularly moved about the sample, the source may be angularly moved, e.g., between 50 and 80 degrees to the sample surface as described in more detail below. The X-ray source may be mounted on a fixed mount (not shown) in embodiments where the X-ray source does not move its angular position or may be mounted on a moveable mount (e.g. on an arm of a goniometer) in embodiments where it is required to move the angular position of the X-ray source. In the latter type of embodiment, on another arm of the goniometer optionally may be mounted the combined detection arrangement.

The X-ray beam from the source interacts with the sample causing both diffraction of the X-ray beam as well as emission of secondary X-rays from the sample. The X-rays from the sample are preferably received along a beam collection axis, i.e. axis 9 shown in FIG. 1. The diffraction angle $\phi$ of the X-rays at the sample is shown in FIG. 1, i.e. the diffraction angle between the irradiation axis and the beam collection axis. The diffracted beam is characteristic of the structure in the sample and the secondary X-ray emission is characteristic of the elemental composition of the sample. The X-rays diffracted and/or emitted from the sample are analysed by means of the combined XRD and XRF detection arrangement 10. The X-rays are received from the sample by the detection arrangement 10 along collection axis 9.

The combined XRD and XRF detection arrangement 10 is a monochromator which comprises a scanning wavelength selector. The wavelength selector is a scanning selector because it is moveable and thus enables a wavelength to be selected at any desired value within the scannable range or enables a wavelength range to be sequentially scanned for XRF measurements, i.e. it enables the X-rays to be monochromated for detection. The combined XRD and XRF detection arrangement is thus a sequential XRF detection channel. The scanning wavelength selector is moveable preferably by means of a driver. This contrasts with prior art designs in which a monochromator for XRD comprises a static wavelength selector which clearly cannot also be used for XRF measurements thus requiring the provision of an additional detection arrangement for XRF. The wavelength selector preferably comprises a wavelength dispersive element. The wavelength dispersive element preferably comprises a diffraction crystal and more preferably a flat crystal. Examples of suitable crystals include any of the following: Lithium Fluoride, Highly Oriented Pyrolytic Graphite (HOPG), Pentaerythritol, Indium Antimonide, Germanium, synthetic multilayer pseudo-crystals, preferably HOPG and multilayers. The wavelength dispersive element preferably is preceded by a collimating element (herein termed an entry collimating element). The entry collimating element is preferably a collimator, herein termed a secondary collimator (thereby distinguishing it from the primary collimator which may be used in front of the X-ray source). In FIG. 1, a secondary collimator 14 is positioned upstream (i.e. nearer the sample) from the dispersive element and thereby defines the collection axis (axis 9 in FIG. 1). More than one entry collimating element (e.g. more than one collimator) may be provided which can be interchangeably positioned in the X-ray beam so as to vary the collimation of the beam. Thus, in use, the X-rays diffracted or emitted from the sample pass along the collection axis through the secondary collimator before being dispersed by the wavelength dispersive element such that only a selected wavelength or wavelengths of X-rays fall on the X-ray detector by the application of Bragg's law at the dispersive element. The wavelength dispersive element preferably is followed by another collimating element (herein termed an exit collimating element), which is positioned before the detector. In cases where there is more than one detector there is typically more than one exit collimating element, preferably one collimating element positioned before each detector. The exit collimating element is preferably a collimator (herein termed a third collimator) positioned between the detector and the wavelength selector as shown in FIG. 1 where a collimator 17 is positioned in front of detector 16 between the crystal 12 and detector 16. The third collimator defines a detector axis 11 to provide angular alignment between the detector and wavelength selector. More than one exit collimating element (e.g. more than one collimator) may be provided which can be interchangeably positioned in the X-ray beam so as to vary the collimating of the beam onto the detector. In FIG. 1, the wavelength selector comprises a crystal 12 as a wavelength dispersive element, a secondary collimator 14 as entry collimating element and a third collimator 17 as exit collimating element. The secondary collimator 14 and third collimator 17 (together with X-ray detector 16) are mounted on either side of the crystal 12 at an angle $\theta$ to the crystal surface. The scanning wavelength selector thus preferably comprises a wavelength dispersive element (e.g. crystal), which is preceded on its X-ray receiving side by an X-ray collimating element (e.g. collimator) and is followed by another X-ray collimating element (e.g. collimator) on its detection side, the X-ray collimating elements preferably being positioned at angle $\theta$ to the surface of wavelength dispersive element. The collimating elements may be mounted on separate arms of a goniometer to enable angle $\theta$ and hence the selected wavelength to be varied. The detector would of course be mounted together with the detector collimating element on the same respective arm of the goniometer. The positioning of the goniometer and hence angle $\phi$ is preferably controlled by an optical encoder. After the X-ray collimating element on the detection side the X-rays, i.e. the monochromated X-rays, are received at the detector. The X-ray detector may comprise any suitable X-ray detector for XRD and XRF known in the art, e.g. a gas filled counter or a scintillation detector or a solid state detector (e.g. a silicon drift detector). Preferably, the detector comprises a gas filled proportional counter.

The scanning wavelength selector is a variable wavelength selector, i.e. it can vary the wavelength which it selects to fall on the X-ray detector. In XRD operating mode, the scanning wavelength selector selects and fixes one or more wavelengths to be detected by the at least one X-ray detector (herein termed fixed wavelengths since they are not varied during XRD pattern acquisition). Preferably, in XRD, the scanning or variable wavelength selector is used or set to the corresponding angle $\theta$ for the selected wavelength(s). That is, for the XRD analysis, angle $\theta$ is kept constant at the angle corresponding to the selected wavelength(s). In XRF operating mode the variable wavelength selector scans through the range of wavelengths which the XRF spectrum is desired to cover, preferably by scanning angle $\theta$, and sequentially selects the wavelengths for detection at the at least one X-ray detector, preferably whilst angle $\phi$ is kept constant (i.e. fixed) throughout the XRF analysis.

The selection of wavelengths of X-rays by the wavelength selector for detection at an X-ray detector 16 can be achieved by different mechanisms. The angle θ at the wavelength dispersive element is variable to select different wavelengths. The invention preferably comprises a driver to vary the diffraction angle θ of the wavelength selector, i.e. the wavelength selector is moveable by a driver to select the wavelengths of X-rays. A driver herein refers to any driving means comprising one or more individual drivers, actuators or the like. Drivers are provided to drive any goniometer of the apparatus. For example, the angle between the collimator 14 and collimator 17 (and hence detector 16) at the crystal 12 can be varied (e.g. by mounting collimator 14 and collimator 17/detector 16 on separate arms of a goniometer) so that the diffraction angle θ at the flat crystal 12 is correspondingly varied. Alternatively, or in addition, the crystal 12 can be rotated to vary θ. In preferred embodiments, as shown in the Figures, the crystal 12 may be positioned at an angle θ to the collimator 14/collection axis 9 with the collimator 17/detector 16 (and thereby detection axis 11) positioned at an angle 2θ to the collection axis 9, e.g. by means of an optical encoder. As the angle θ is changed e.g. by moving the collimator 14 and/or the crystal 12 (e.g. by means of drivers driving a goniometer), the collimator 17/detector 16 are synchronously moved to maintain an angle 2θ (e.g. again by means of drivers driving a goniometer) so that different wavelengths are diffracted at different angles and are detected by the detector 16. For XRD, θ is preferably set (fixed) for the duration of the XRD measurement so that at least one wavelength of emission from the X-ray source is chosen (fixed) to pass onto the detector (the angle φ is then varied for the XRD measurement and the detector detects X-rays of the selected fixed wavelength(s) for one or more different values of diffraction angle φ at the sample).

The diffraction angle of the X-rays diffracted from the sample may be termed herein a first diffraction angle, φ. This term may be used to distinguish the first diffraction angle, φ, from a diffraction angle of X-rays from a crystal of the wavelength selector, which may be termed herein a second diffraction angle, θ.

The angle φ can be varied for XRD by one or more of the following methods:

by angularly moving (e.g. rotating) the combined XRD and XRF detection arrangement 10 about the sample, e.g. along arcuate direction 18 in FIG. 1;

by angularly moving (e.g. rotating) the X-ray source about the sample, e.g. along arcuate direction 20 in FIG. 1;

by angularly moving (e.g. rotating) or tilting the first collimating element (primary collimator 6) relative to the sample.

Any one or more of the above methods i), ii) and/or iii) may be used alone or in any combination, for example a combination of i) and ii), or a combination of i) and iii), or a combination of i), ii) and iii) etc.

An economical method is iii) above but tilting the primary collimator alone can achieve only limited resolution and angular range. However, a limited angular range of scanning φ may be adequate for some uses, e.g. where the user wishes only to analyse a sample for a specific structural phase, e.g. free lime phase in a cement sample. Combining i) and ii) offers the most flexible method which gives the widest range of diffraction angles φ and good resolution. Moving the X-ray source gives the additional advantage of being able to tune the penetration depth inside the sample. However providing a mechanism to accurately move the X-ray source, which can be heavy, adds to the cost and complexity and so in preferred embodiments, from the viewpoint of a compromise between flexibility and cost the angle φ is variable by means of method i) above. The invention preferably comprises a driver to vary the diffraction angle φ at the sample.

When angularly moving the combined XRD and XRF detection arrangement 10 this changes the angle which the X-ray collection axis 9 makes with the irradiation axis 8, i.e. changes the collection angle, and hence changes the diffraction angle φ at which detection is made. Similarly, when angularly moving the X-ray source and/or the primary collimator this changes the angle which the irradiation axis 8 makes with the collection axis 9, i.e. changes the irradiation angle, and hence changes the diffraction angle φ at which detection is made.

Numerous variations of the apparatus shown in FIG. 1 can be implemented which provide different mechanisms for varying the first diffraction angle φ at the sample for XRD measurements. Examples of such variations are now described.

Figure 2:
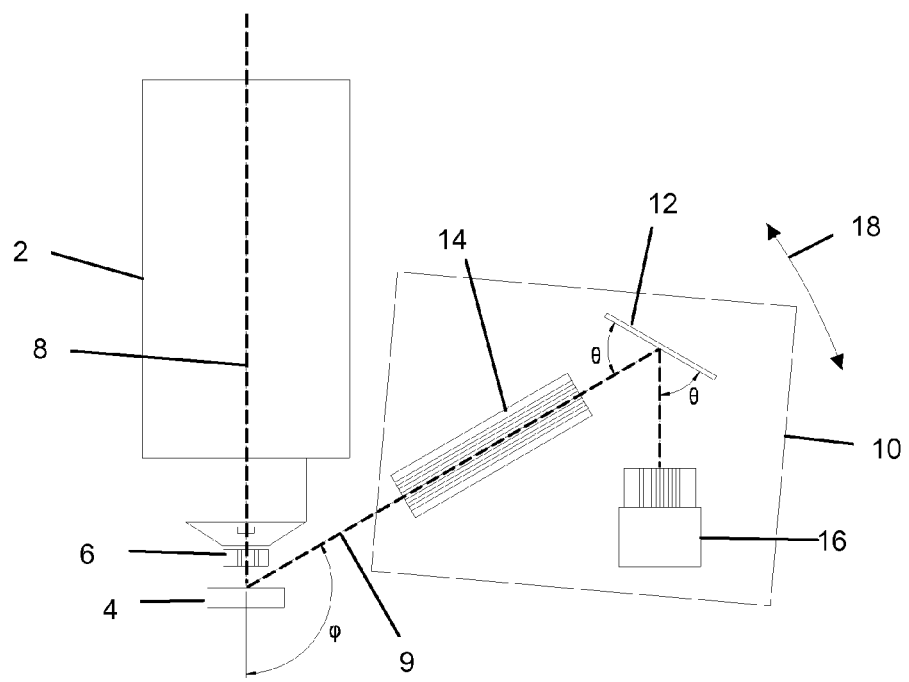
FIGS. 2 to 5 show schematically side views of various further embodiments of apparatus according to the present invention illustrating different methods for varying the diffraction angle for XRD measurements.

A first variation of apparatus, implementing method i) above, is shown schematically in FIG. 2, wherein an apparatus generally as shown in FIG. 1 comprises an X-Ray tube 2 and primary collimator 6 which are fixed with respect to the sample 4 thus fixing irradiation axis 8 and the diffraction angle φ is scanned by angularly moving the detector arrangement 10 (i.e. secondary collimator 14, crystal 12, collimator 17 and detector 16 jointly) in an arcuate direction 18 thus varying the angle of the collection axis 9 with respect to the sample. The irradiating beam axis can be at an angle different than normal to the sample. For illustration only, the X-Ray tube 2 is shown mounted normally with respect to the sample 4 (i.e. irradiation axis normal) but in practice this need not be the case and indeed it may be preferable to mount the tube at an angle to the sample to make available a greater range of angular movement to the detection arrangement 10 in turn permitting access to additional crystalline structures and thereby more complete structural determination. Another reason to mount the tube at an angle to the sample is to allow more space for the combined XRD/XRF detection arrangement and to allow the tube to be positioned closer to the sample to thereby achieve a greater signal from the sample. The combined detector arrangement 10 may comprise, for example, a goniometer, i.e. with secondary collimator 14 and the X-ray detector 16 on opposite arms of the goniometer so that the angle θ may be varied at the crystal 12. In the apparatus variation shown in FIG. 2, the entire goniometer of the detection arrangement may then be angularly moved with respect to the sample, e.g. by means of a driver (not shown), to vary diffraction angle φ between beam axes 8 and 9. The invention thus preferably comprises a driver to vary the diffraction angle φ at the sample. The invention more preferably comprises a driver for controlling angular movement of the combined detection arrangement so as to vary diffraction angle φ at the sample.

Figure 3:
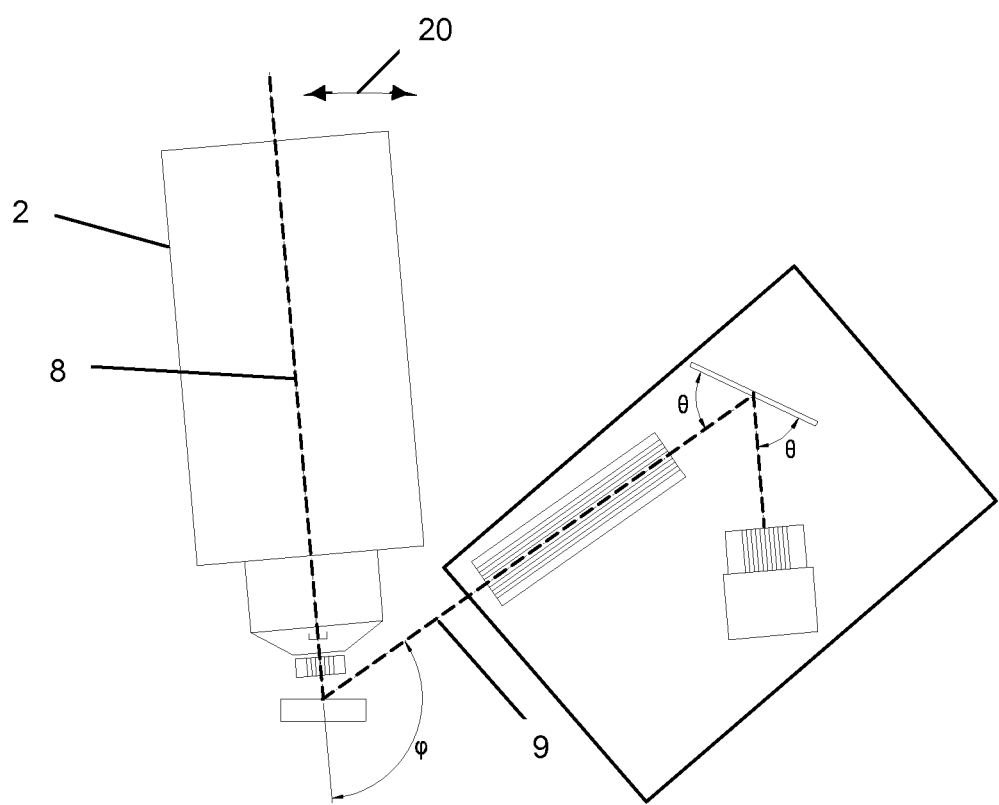

A second variation of apparatus, implementing method ii) above, is shown schematically in FIG. 3, wherein an apparatus generally as shown in FIG. 2 is illustrated but, in this variation, the combined detection arrangement 10 is angularly fixed with respect to the sample, thus angularly fixing collection axis 9 and instead the X-ray source 2 and primary collimator 6 (and hence irradiation axis 8) are jointly angularly moveable about the sample (e.g. by means of a driver not shown in the Figure) e.g. along arcuate direction 20 shown to vary the diffraction angle φ.

Figure 4:
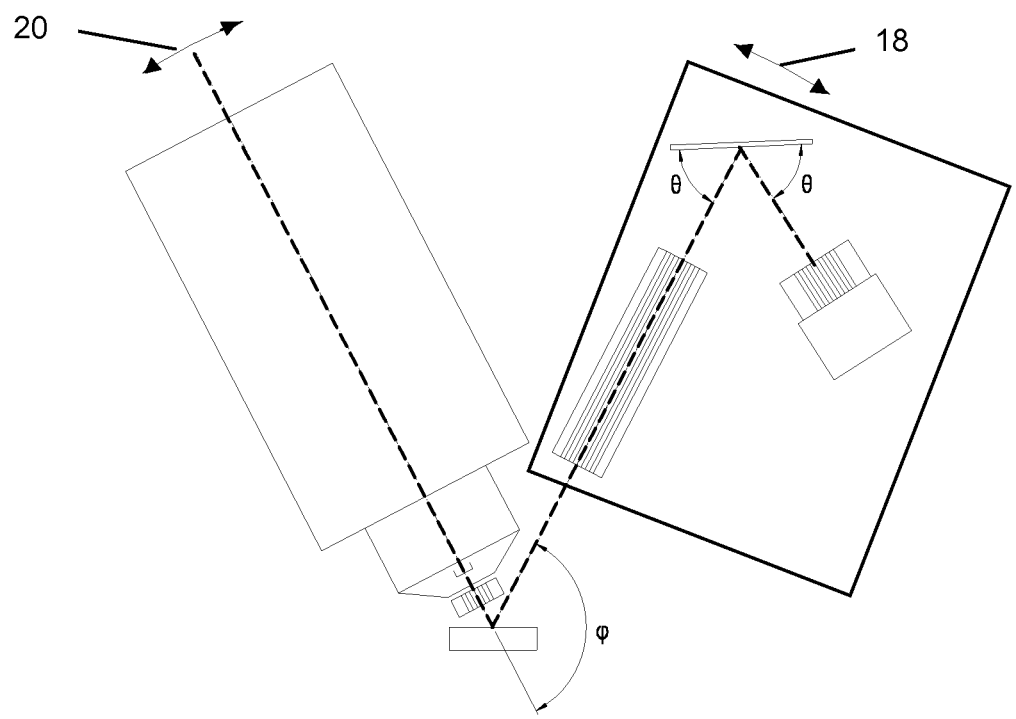

A third variation of apparatus, implementing both of the movement mechanisms shown in FIGS. 2 and 3, is shown schematically in FIG. 4, wherein an apparatus generally as shown in FIGS. 1 to 3 is illustrated but, in this variation, both the combined detection arrangement 10 and X-ray source 2 (with primary collimator) are each angularly moveable about the sample (e.g. along respective arcuate directions 18 and 20) to vary the diffraction angle φ. For example, the combined detection arrangement 10 and X-ray source 2 (with its primary collimator) may be mounted on separate arms of a goniometer (not shown) to vary the diffraction angle φ at the sample. This variation offers the greatest degree of scanning of the diffraction angle φ at the sample.

Figure 5:
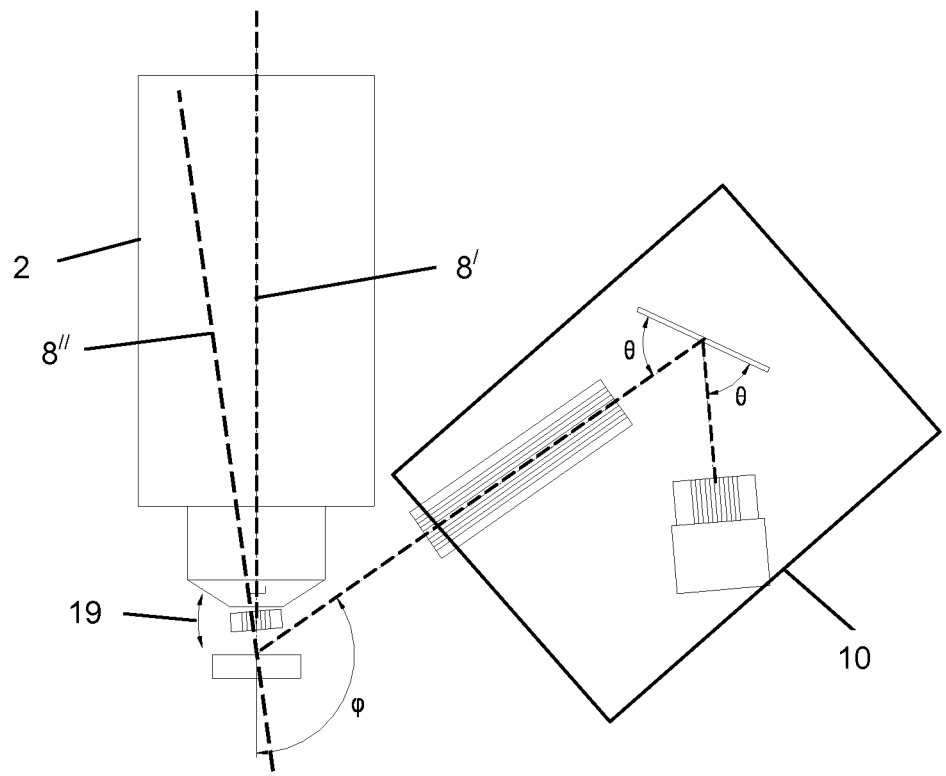

A fourth variation of apparatus, implementing method iii) above, is shown schematically in FIG. 5, wherein an apparatus generally as shown in FIGS. 1 to 4 is illustrated but, in this variation, both the X-ray source 2 and the combined detection arrangement 10 are angularly fixed with respect to the sample and the diffraction angle φ at the sample is varied by tilting the primary collimator 6, e.g. in direction 19 shown, to vary the angle of irradiation axis 8 of the beam at the sample. FIG. 5 shows both the alignment (8') of the irradiation axis 8 when the primary collimator 6 is not tilted and the alignment (8") of the irradiation axis 8 when the primary collimator 6 is tilted.

In some embodiments, the sample may be angularly moveable, such that it can be rotated or tilted, e.g. with respect to the irradiation axis and/or collection axis, thereby to access different planes of crystallites at different depths inside the sample and also to reduce the X-Ray beam path length inside the sample and hence the absorption. The holder for the sample in such embodiments accordingly may be driven by drivers to move the sample holder and sample supported thereon. It is preferable that the sample holder is removable from the apparatus so that the sample may be changed.

Figure 6:
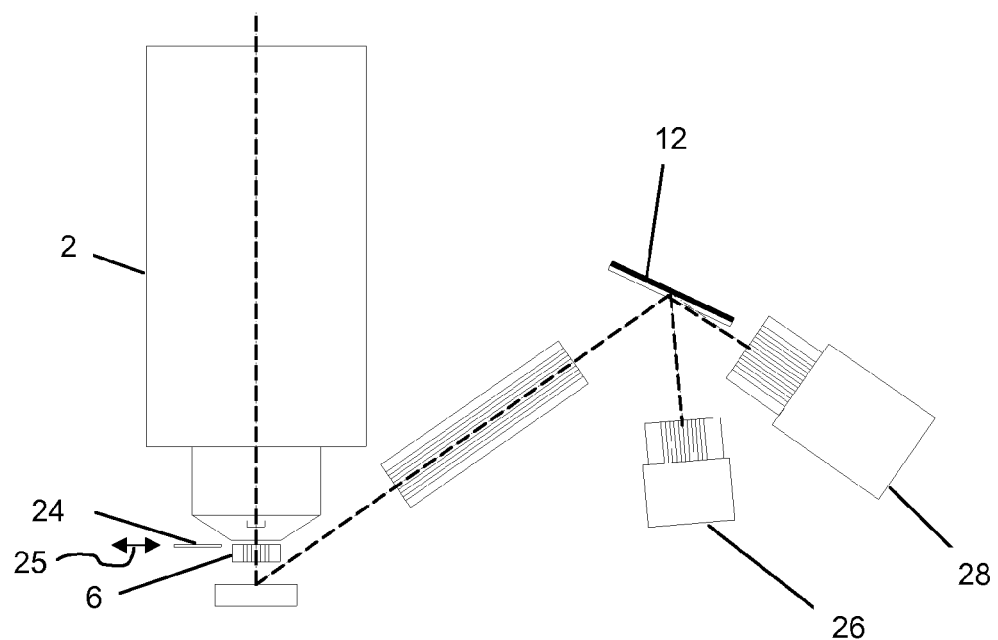
FIG. 6 shows schematically a side view of another embodiment of an apparatus according to the present invention comprising multiple X-ray detectors.

The combined XRD and XRF detection arrangement comprises an X-ray detector, which means that it comprises at least one X-ray detector. In preferred embodiments from the view point of cost and simplicity only one X-ray detector may be employed and this is adequate. However, in more sophisticated embodiments, two or more X-ray detectors may be employed, for example to extend the accessible XRF wavelength range or to improve the XRD measurement. Each detector may have optimum sensitivity for a specific X-ray wavelength range in order to improve performance. For example, for the lower energy ranges of the spectrum preferably gas detectors such as flow proportional counters (FPC) or sealed detectors are used and for higher energy ranges of the spectrum other detectors like scintillators are preferred. An example of such an embodiment with multiple detectors is shown schematically in FIG. 6. In FIG. 6 an apparatus is shown, which is otherwise as shown in FIGS. 1 to 5, and which has in place of the single detector 16 two X-ray detectors 26 and 28 having different spectral sensitivities, each optimized for a given portion of the spectrum. One detector is employed for the low energy range of the X-ray fluorescence spectrum (long wavelength) corresponding to a given range of θ for a given crystal and the other detector is employed for the high energy range (short wavelength) corresponding to another given range of θ. During measurements, preferably one detector is used at a time to detect X-rays over the θ angles corresponding to the optimum wavelength range for that detector, and the other detector is subsequently used to detect X-rays of another spectral range, where it is more sensitive than the first one. The wavelength selector of the detection arrangement is thus arranged in such embodiments to select more than one fixed wavelength, in this case two fixed wavelengths, e.g. in order to select more than one single X-Ray emission line of the X-ray tube for XRD. Thus, each detector could be selected to detect a different characteristic emission line of the tube. This allows the possibility of improving the sensitivity in XRF analysis and accessing additional diffraction phases in XRD analysis. In such embodiments, each detector may be arranged to detect X-rays from its own wavelength selector or dispersing element (e.g. crystal) or two or more detectors may share the use of a common wavelength selector. There are crystals, e.g. LIF200, which can be used for both low and high energy detectors, but there are also crystals which should be used only at low (or high) energy. In practice it may be advantageous therefore to switch from one crystal-detector pair to another when changing the energy range of the analysis. The different crystals may be mounted on a rotating turret to allow switching from one to another.

In preferred embodiments, one or more spectral filters can be incorporated between the X-ray source and the sample to improve the XRF or XRD performance as known in the art. For example, filters may be used for XRF analysis to suppress characteristic lines emitted by the X-ray tube which could interfere with the wavelengths to be analysed (eg. Cu filter to suppress Rh lines etc.). Filters may also be used to minimize the spectral background due to the continuum in samples where heavy elements are embedded in a light matrix (eg. Al filter to analyse Pb etc.). For XRD, filters may be used, for example, to select (monchomatise) one line of interest emitted by the tube. In FIG. 6 a filter 24 is shown which can be reciprocally moved in the lateral direction 25 in and out of the X-ray beam between the X-ray source 2 and the primary collimator 6.

The X-ray source, which is preferably an X-ray tube, may have one or a plurality of characteristic emission lines. For the purpose of having more than one emission line, the X-ray tube may include a plurality of anodes of different materials or a multiple anode. Common anodes include a target material of one of the following (for example): Rh, Pd, Cr, Mo, W, Sc, Cu, Pt and Au. The choice of target material is, of course, determined by the nature of the sample to be analysed. This feature enables the apparatus to extend the XRD measurements or improve the XRF capabilities. Where a plurality of emission lines of the X-ray source are present, a plurality of these emission lines may be selected as the fixed wavelengths for XRD analysis as described above.

For the XRD measurement, in some preferred embodiments the wavelength selector can be sequentially positioned in order to select more than one single X-Ray emission line of the tube, i.e. more than one XRD pattern can be recorded sequentially based on different X-Ray emission lines. In other words, two or more XRD patterns may be recorded sequentially, each using a different fixed wavelength. This allows access to other diffraction phases.

The combined XRD and XRF detection arrangement may comprise more than one wavelength dispersive element, e.g. more than one crystal, to extend the wavelength range for XRF or to improve the XRD measurement. In some embodiments, therefore, a plurality of crystals may be provided which can be interchanged in the detection arrangement, e.g. by automated interchanging means.

The apparatus preferably comprises a chamber in which is housed the other components of the apparatus, e.g. the X-ray source, the sample holder, combined XRD and XRF detection arrangement and angular scanning means, wherein the chamber can be evacuated and/or flushed with gas which is substantially spectrally transparent at the wavelengths to be detected, more preferably wherein the chamber is evacuable.

In use, the apparatus of the present invention can be operated in either of two modes:

XRD measurement mode: wherein the angle θ of the wavelength selector is fixed at the value corresponding to the selected fixed wavelength(s) of interest for optimum XRD performances and the intensity of the diffracted X-rays are measured by the detector at one or more values of φ, e.g. angle φ is varied to scan the diffraction angle at the sample. Since the wavelength of X-rays detected in XRD mode is fixed, with the X-rays from the source being parallel, this allows application of Bragg's law to perform the XRD measurement; and XRF measurement mode: wherein the angle θ of the wavelength selector is varied to scan the wavelengths of interest of the secondary fluorescence X-rays emitted from the sample and their intensities are measured using the X-ray detector(s). Thus, state of the art XRF measurements may be performed sequentially (the angle φ at the sample being typically fixed for the duration of the XRF measurement).

For XRF analysis of a sample it may be desirable in some cases to record XRF spectra at different values of angle φ. There are two potential benefits of changing the angle φ. Firstly, varying φ allows the user to tune the penetration depth of X-Rays inside the sample. For example, in extreme cases, the XRF analysis could be performed at grazing incidence to the sample surface in order to probe thin layers on top of the sample. Secondly, varying φ allows the user to reduce eventual interferences due to diffraction of the continuum by the sample by choosing a particular value of angle φ in order to further distance such interferences from the peaks of interest in the XRF spectrum.

The apparatus thus uses a single detection arrangement for performing both XRD and XRF and, moreover, uses only one X-ray source. This offers several advantages in terms of compactness and using a minimum number of components while keeping a high level of versatility regarding the range of materials to be analyzed.

The invention provides an advantageous method and apparatus for analysing the elemental and structural composition of a sample, especially a crystalline sample. The term crystalline sample herein means a sample of which at least a part is crystalline, i.e. the crystalline sample may be wholly or partially crystalline. The sample to be analyzed may be polycrystalline, i.e. comprising crystallites which are isotropically and randomly distributed in the sample. It will be appreciated that a sample to be analysed by the apparatus of the invention may be amorphous, in which case only XRF is useful in analysing the sample. The XRD analysis enables the crystalline structure within the sample to be analysed. The XRF analysis enables the elemental and/or chemical composition of the sample to be determined. As an example, the apparatus of the present invention may be useful in the analysis of cement samples in which, in addition to the elemental and chemical composition, it is also desirable to determine the content of the various structural forms of calcium oxides such as free lime as well as other phases.

The XRD analysis is performed by selecting and fixing the wavelength of diffracted X-rays using the wavelength selector of the combined XRD and XRF detection arrangement. With the wavelength of diffracted X-rays fixed by selection, the angle φ is varied and for maximum angular scanning this is preferably done by angularly moving either of or both the X-ray source (which includes a concerted movement of a primary collimator of the source) and the combined XRD and XRF detection arrangement about the sample, i.e. moving either of or both of these at least partially around the sample, to allow detection of the diffracted X-rays of the selected wavelength at different diffraction angles φ.

In some embodiments, the diffraction angle at the sample φ may be fixed so that the XRD intensity of the selected wavelength(s) selected by the scanning wavelength selector is detected only for one fixed value of φ. However, the fixed value of φ is preferably established to correspond to a known XRD peak of a particular structural phase to be detected. In other words, the detection is made at a tuned position centered on the maximum of a diffraction peak of interest. In such embodiments, the apparatus is thereby dedicated, from an XRD perspective, of analysing for one particular structural phase but maintains full XRF scanning capability.

In simple preferred embodiments, the angle φ is variable by a small extent, e.g. +/−4 degrees or less in order to scan over a single XRD peak of interest, e.g. the free lime XRD peak only. For free lime applications in the cement industry, the centre of the peak position can vary depending on several parameters related to the sample structure so it is not preferably to absolutely fix the angle φ but rather to have at least some variability for φ. For the simplest embodiments with limited variation in the value of φ, the φ angle is preferably varied by tilting the primary collimator in front of the X-ray source.

For more sophisticated embodiments which would cover other applications in XRD than just a single XRD peak such as free lime, a wider φ variation is required and the further means described herein for varying φ are preferably employed. An XRD pattern may then be recorded.

The XRF analysis is performed by scanning wavelengths of X-rays emitted by the sample using the wavelength selector and detecting X-rays of the scanned wavelengths using the X-ray detector. The XRF technique performed using the combined XRD and XRF detection arrangement is therefore wavelength dispersive XRF (WDXRF). WDXRF is advantageous compared to energy dispersive XRF (EDXRF) because of the high spectral resolution, high dynamic range, good stability and flexibility of WDXRF as well as increased sensitivity depending on the number of wavelengths to be measured. In the XRF analysis the diffraction angle φ at the sample is preferably fixed, i.e. so that the combined XRD and XRF detection arrangement does not angularly move relative to the sample during XRF analysis.

In certain preferred embodiments, e.g. for reduction of cost, the apparatus of the invention comprises no other XRF detection channel, i.e. no other XRF or XRD detection channel or arrangement than the combined XRD and XRF detection arrangement. The sequential XRF detection provided by the combined XRD and XRF detection arrangement is efficient for detection of all common XRF wavelengths. If speed of XRF analysis is a critical factor for a user, the apparatus of the invention can further comprise one or more additional XRF detection channels. Such one or more additional XRF channels may comprise one or more static XRF channels (i.e. for detection of a fixed X-ray wavelength) or a sequential XRF channel (i.e. for detection of variable X-ray wavelength).

For a fixed position of the X-ray source and combined detector arrangement, i.e. fixed diffraction angle at the sample φ, scanning the wavelength (angle θ) in the continuum range allows directly extraction of a diffraction spectrum since, according to Bragg's law, the lattice dimension is related to both the diffraction angle and to the wavelength of the X-rays. Therefore, by irradiating with a continuum of wavelengths at fixed diffraction angle, the diffraction pattern can be obtained by recording the diffracted intensity vs. wavelength.

It will be appreciated that he selection of either XRD or XRF mode and the corresponding required movement of components for each mode as described above, e.g. via drivers and/or goniometers, is preferably under the control of a computer. The same or another computer is preferably also provided for acquiring data from the combined detection arrangement for subsequent output, e.g. as an XRD pattern or XRF spectrum.

Figure 7:
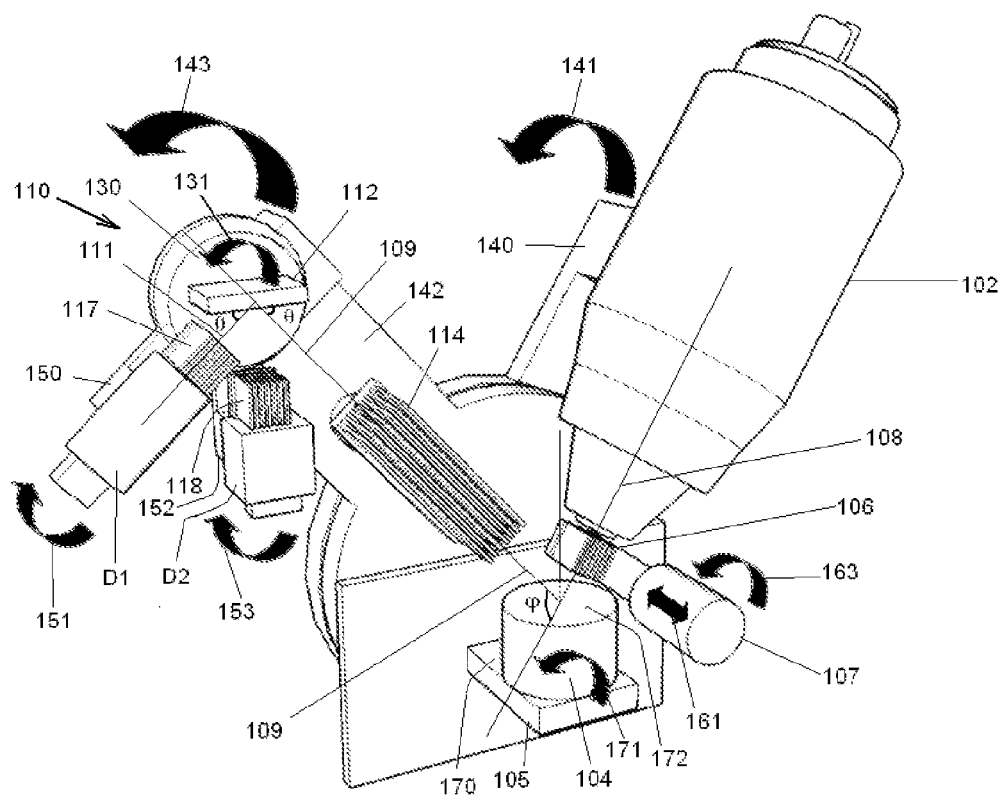
FIG. 7 shows schematically a perspective view of an embodiment of the present invention which illustrates some of the possible modes of movement of the components and possible mounting arrangements.

Further exemplary embodiments of the invention are shown in FIGS. 7 to 14. FIG. 7 shows a schematic perspective view of an embodiment of the present invention which illustrates many of the possible modes of movement. In practice, any given embodiment of the invention could include all of these modes of movement or less than all of them (i.e. only some of them) as will be appreciated from the description of the invention herein. FIG. 7 shows generally an X-ray source 102 for irradiating a sample 104 mounted on the upper surface 170 of a sample holder 105 with X-rays as previously described. The X-rays may pass through a primary collimator 106 which is laterally retractable into and out of the X-ray beam in the direction of arrow 161 shown. The primary collimator 106 can also be tilted with respect to the sample surface by limited rotation of the collimator 106 in the direction shown by arrow 163. Such tilting of the axis of the primary collimator 106 changes the angle of incidence of the irradiation axis on the sample surface 172 and hence changes the diffraction angle φ at the sample as described above. The sample holder 105 can also be tilted with respect to the incident X-rays to permit access to different crystal planes in the sample. Tilting of the sample holder 105 is represented by the arrow direction 171. The X-ray source 102 is mounted on a goniometer arm 140 of a goniometer for varying the diffraction angle φ at the sample. On the other arm 142 of the goniometer for varying φ is mounted the combined XRD and XRF detection arrangement shown generally at 110. In use, the goniometer arms 140 and 142 can be moved in the arcuate directions as shown by the arrows 141 and 143 in order to vary the diffraction angle φ at the sample (of course movements indicated by arrows in the Figures also include movements in the opposite direction, i.e. the movement of components is reversible). In the Figures herein, the goniometer drivers are omitted for convenience as is the controlling computer and associated control elements for controlling goniometer operation. However, the drivers and computer control elements may simply be of any known type suitable for controlling goniometer movement. The detection arrangement 110 comprises a monochromator which has an entry collimator 114 of the Soller type (defining X-ray collection axis 109), a flat crystal 112 for dispersing the X-rays and, in this case, two X-ray detectors D1 and D2, each of which has a respective collimator 117 and 118 in front of it (defining a detection axis 111), which are also of the Soller type. The detectors D1 and D2 each have a sensitivity optimised for different wavelength ranges. The crystal 112 is mounted on a rotatable mount 130 in order that the crystal 112 can be rotated in the direction shown by arrow 131 in order to vary the angle θ at the crystal 112. For varying the angle θ at the crystal 112, in addition to the crystal motion described, the detectors D1 and D2 are each also mounted on respective goniometer arms 150 and 152 for movement in the arcuate directions shown respectively by arrows 151 and 153. The goniometers 150, 152 on which the detectors are mounted are, in turn, mounted on the goniometer arm 142 on which the whole combined XRD and XRF detection arrangement is mounted.

The operation of the apparatus for XRF and XRD will now be explained more fully with reference to FIGS. 8 to 14.

Figure 8:
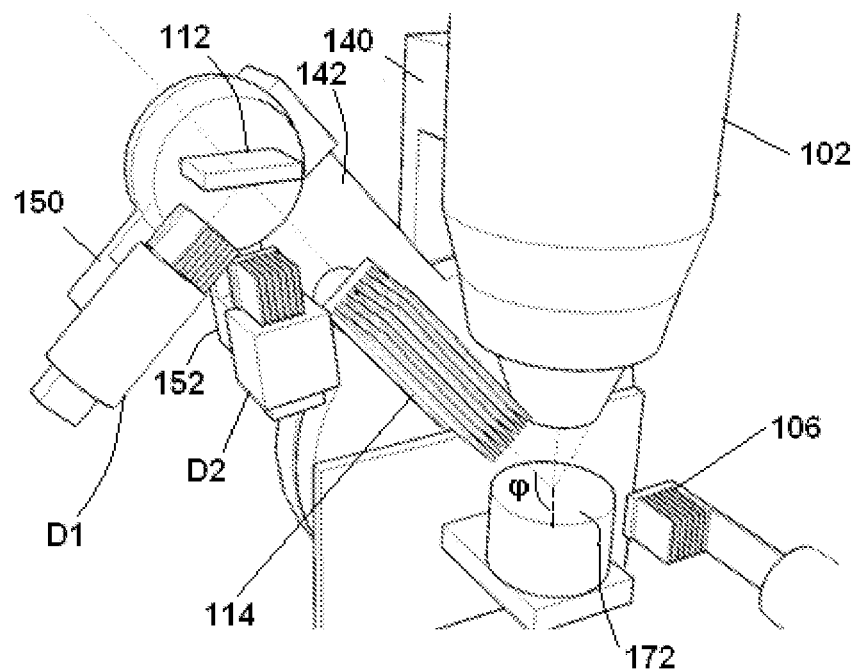
FIGS. 8 and 9 show schematically perspective views of an embodiment of the invention illustrating operation for XRF analysis using a first detector.
Figure 9:
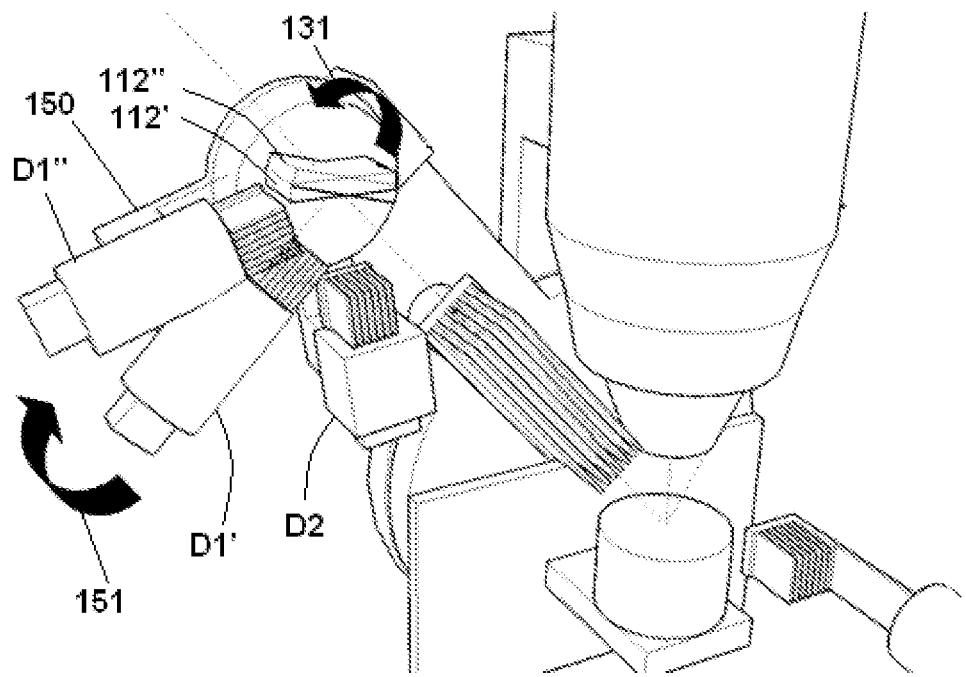
Figure 10:
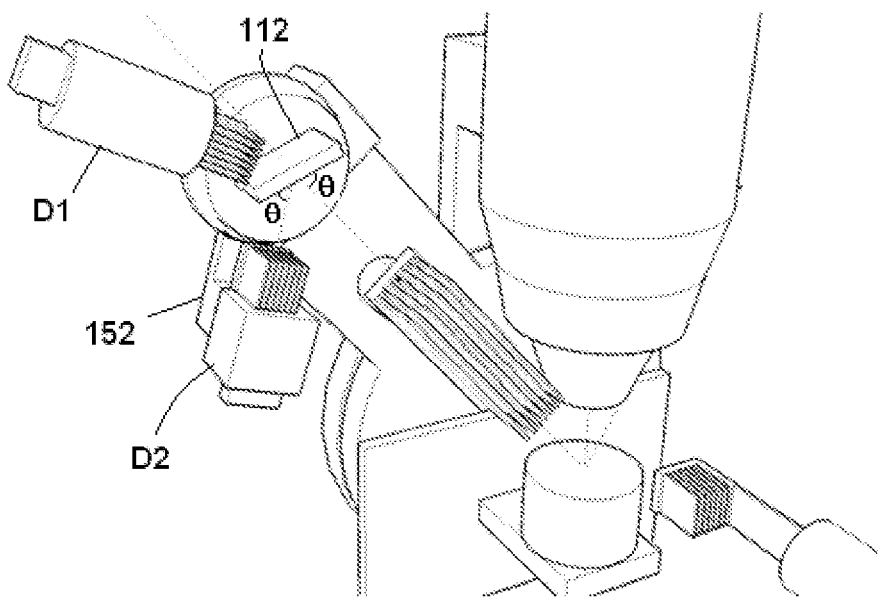
FIG. 10 shows a similar view to FIGS. 8 and 9 but illustrating operation for XRF analysis using a second detector.

Referring to FIGS. 8 and 9 there is shown an apparatus similar to that shown in FIG. 7 illustrating the operation for XRF analysis. In this embodiment, for XRF, the X-ray tube 102 is shown mounted normally to the sample surface 172 to allow for improved sample illumination. The primary collimator 106 is retracted out of the X-ray beam for the XRF measurement in order to increase sensitivity. The diffraction angle φ at the sample is fixed for the XRF operation by setting the goniometer 140, 142 to an appropriate angle under computer control. With φ fixed, the sample is irradiated with X-rays from the X-ray tube 102 along irradiation axis 108 causing emission of secondary X-rays. The secondary X-rays enter collimator 114 and the collimated X-rays are then dispersed according to their wavelength by the flat crystal 112. In FIG. 8 the apparatus is shown with the combined detection arrangement set so that the detector D1 receives the X-rays dispersed from the crystal 112, i.e. the crystal 112 is rotated under computer control to such an angle and goniometer arm 150 is set to such an angle that detector D1 receives dispersed X-rays of a desired wavelength according to a first value of angle θ at the crystal. In practice, detector D1 is optimised to detect X-rays in a first wavelength range and detector D2 is optimised to detect X-rays in a second wavelength range, typically complementary to the first wavelength range. In order for the detector D1 to scan the intensity of the X-rays across a range of wavelengths, the crystal 112 and goniometer 150 are angularly moved as shown by arrows 131 and 151 respectively to vary θ. FIG. 9 shows the positions of the crystal 112 at a first position 112' and correspondingly the detector D1 at a first position D1' thereby permitting detection of X-rays of a first wavelength, corresponding to a first value of θ. Then the crystal 112 is moved to a second position 112" and correspondingly the detector D1 is moved to a second position D1" thereby permitting detection of X-rays of a second wavelength, corresponding to a second value of θ. The crystal and detector are then moved to appropriate corresponding third, fourth etc. positions to sequentially detect the intensity of secondary X-rays across the desired range of wavelengths as θ is varied. The detected X-ray intensities are sent as signals from the detector to a computer (which also receives angular position information for determination of θ and hence detected wavelength) for data processing and/or storage and/or output, e.g. as an XRF spectrum. Whilst use of a single X-ray detector may be adequate for many applications, in some cases in order to cover a particular wavelength range with optimum sensitivity it may be useful to employ a second detector such as detector D2 shown in FIGS. 7 to 10 having optimised sensitivity for a wavelength range of interest. As shown in FIG. 10, after detection across the wavelength range optimised for detector D1, the detector D1 is moved by means of its goniometer 150 out of the way of detector D2's range of movement. The crystal 112 is then set to disperse X-rays of the appropriate wavelength for detection by detector D2. Scanning of wavelengths by detector D2 is then carried out in an analogous manner to that described above for detector D1 by moving the crystal 112 and detector goniometer 152 to vary θ for detector D2.

Figure 11:
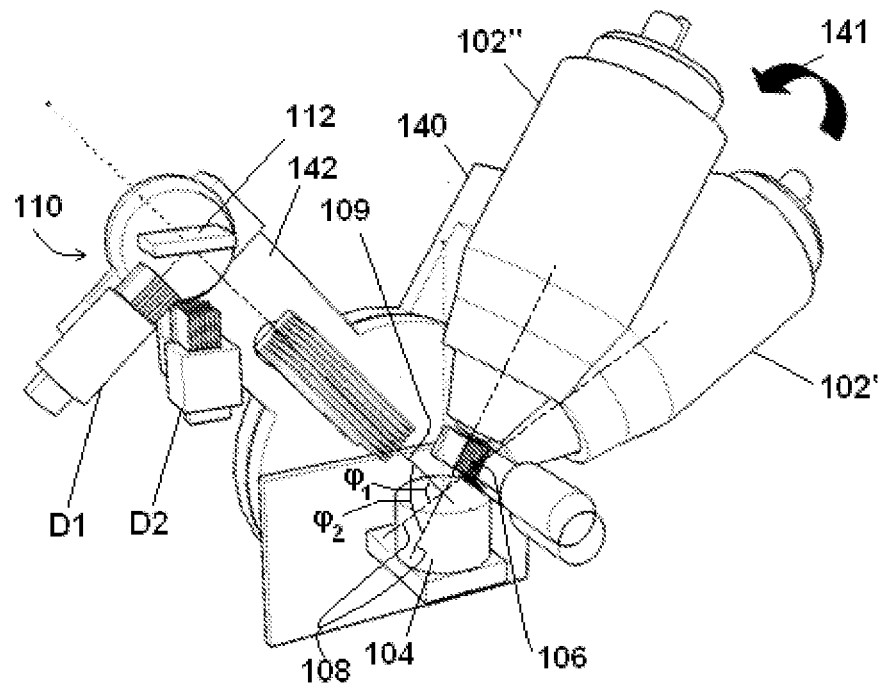
FIGS. 11 to 15 show schematically perspective views of embodiments of the invention illustrating various modes of operation for XRD analysis.
Figure 12:
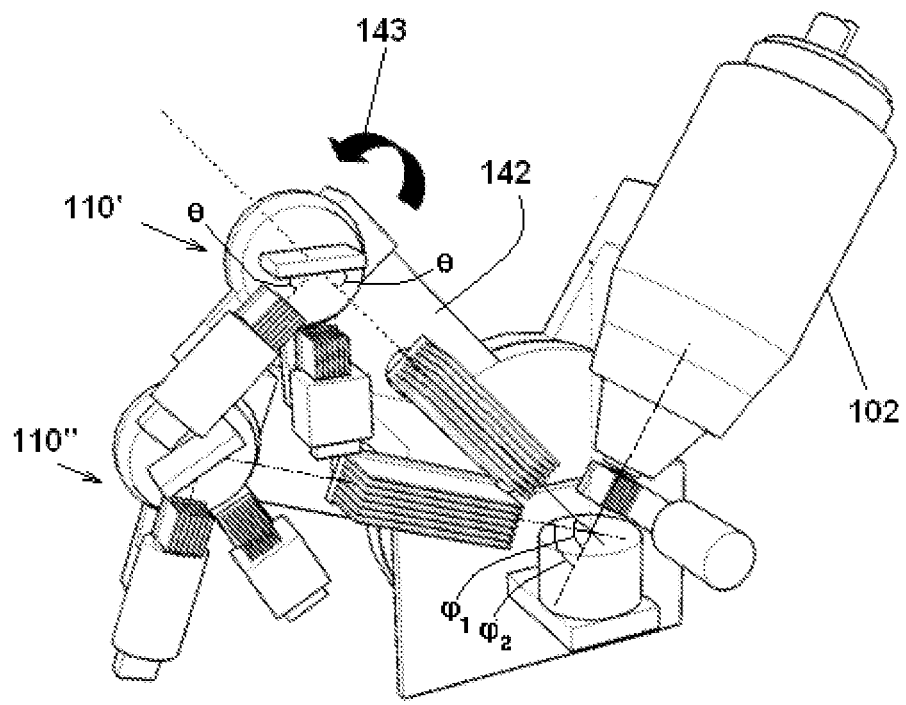
Figure 13:
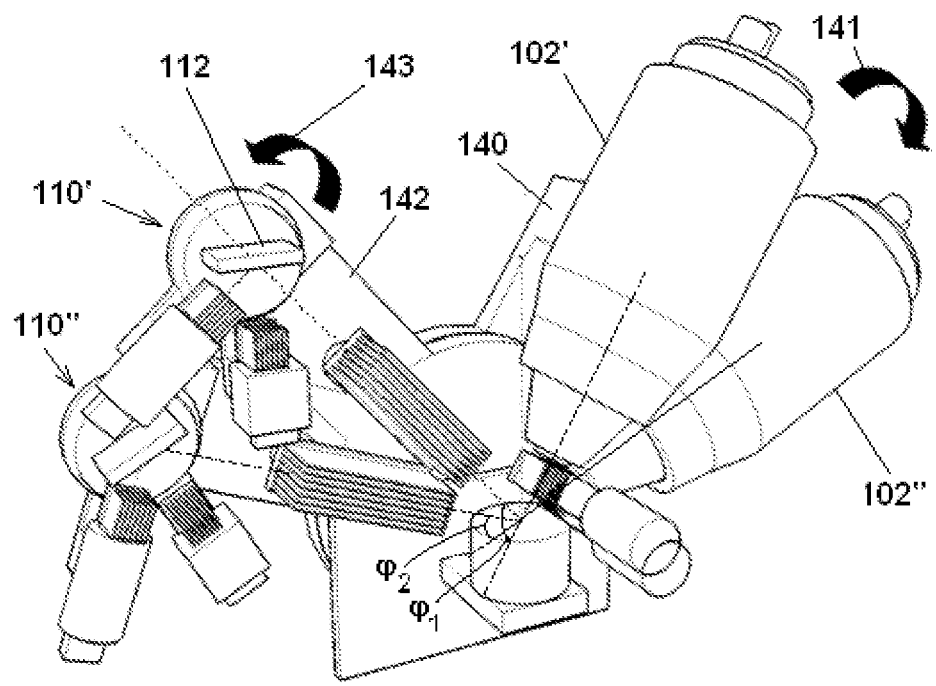

Referring to FIGS. 11 to 13 there is shown an operation of the apparatus shown in FIGS. 8 to 10 for XRD analysis. With reference to FIG. 11 first of all, the combined XRD and XRF detection arrangement 110 is adjusted to a suitable diffraction angle θ at the crystal 112 so that X-rays of a characteristic wavelength of the X-ray tube 102 are sent to detector D1 (or alternatively D2). The angle θ set in this way to the diffracted X-ray wavelength then remains constant throughout the XRD analysis. The X-ray tube 102 is preferably positioned, as shown, at an angle to the collection axis 109 by suitable angular setting of goniometer arm 140. The primary collimator 106 is positioned in the X-ray beam from the X-ray tube so as to collimate the beam irradiating the sample surface and enable definition of the diffraction angle φ at the sample. The combined detection arrangement 110 is also set at an angle to the sample by goniometer arm 142 as shown. The diffraction angle φ at the sample defined by the irradiation axis 108 and collection axis 109 is shown in FIG. 11. A first diffraction angle $\phi_1$ is set when the X-ray tube is in a first shown angular position 102'. The sample is irradiated with X-rays from the tube 102 whilst the tube is in the first position. X-rays of the wavelength set by the combined XRD and XRF detection arrangement 110 are diffracted by the sample and the intensity of the X-rays are detected by the detector D1. The X-ray tube is then moved by movement of goniometer arm 140 in direction 141 to a second angular shown position 102" thereby defining second diffraction angle $\phi_2$. The collimator 106 moves in concert with the X-ray tube 102. The X-ray tube 102 (and its primary collimator 106) is then moved to appropriate corresponding third, fourth etc. angular positions to sequentially detect the intensity of diffracted X-rays of the fixed wavelength across the desired range of diffraction angle $\phi$. The detected X-ray intensities are sent as signals from the detector to a computer (which also receives angular position information for determination of $\phi$) for data processing and/or storage and/or output, e.g. as an XRD pattern (i.e. X-ray intensity versus $\phi$).

With reference to FIG. 12, the combined XRD and XRF detection arrangement 110 is again adjusted to a suitable diffraction angle $\theta$ at the crystal 112 so that X-rays of a characteristic wavelength of the X-ray tube 102 are sent to detector D1 as shown (or alternatively D2) and the angle $\theta$ set in this way remains constant throughout the XRD analysis. However, in contrast to the operation mode described with reference to FIG. 11, the operation mode illustrated by FIG. 12 involves the first diffraction angle $\phi_1$ being set with the X-ray tube 102 in a fixed position and with the combined XRD and XRF detection arrangement 110 in a first shown angular position 110'. The sample is irradiated with X-rays from the tube 102 whilst the detection arrangement is in the first position 110'. X-rays are diffracted by the sample and the intensity of the X-rays of the wavelength set by the detection arrangement 110 is detected by the detector D1. The detection arrangement 110 is then moved by movement of goniometer arm 142 in direction 143 to a second shown angular position 110" thereby defining second diffraction angle $\phi_2$. The detection arrangement 110 is then moved to appropriate corresponding third, fourth etc. angular positions to sequentially detect the intensity of diffracted X-rays of the fixed wavelength across the desired range of diffraction angle $\phi$. The detected X-ray intensities are processed etc. as described before using the computer (not shown).

It will be appreciated that the methods and means for varying the diffraction angle $\phi$ at the sample for XRD shown in FIGS. 11 and 12 may be employed together as shown in FIG. 13. In this embodiment, yet again, the combined XRD and XRF detection arrangement 110 is adjusted to a suitable diffraction angle $\theta$ at the crystal 112 so that X-rays of a characteristic wavelength of the X-ray tube 102 are sent to detector D1 as shown (or alternatively D2) and the angle $\theta$ set in this way remains constant throughout the XRD analysis. The X-ray tube 102 and the combined detection arrangement 110 in this case are set to respective first angular positions 102' and 110' by means of their respective goniometer arms 140 and 142. A first diffraction angle, $\phi_1$, at the sample 104 is thereby defined. X-rays from the X-ray tube are diffracted by the sample and detected by the detector D1 at $\phi_1$. Next, the X-ray tube 102 and the combined detection arrangement 110 are set to respective second angular positions 102" and 110" by means of their respective goniometer arms 140 and 142, such that a second diffraction angle, $\phi_2$, at the sample is thereby defined and the diffracted X-rays are again detected by the detector D1, this time at $\phi_2$. The X-ray tube 102 and the combined detection arrangement 110 are subsequently set to respective third, fourth etc. angular positions so that the XRD pattern may be acquired over a range of diffraction angle $\phi$.

Figure 14:
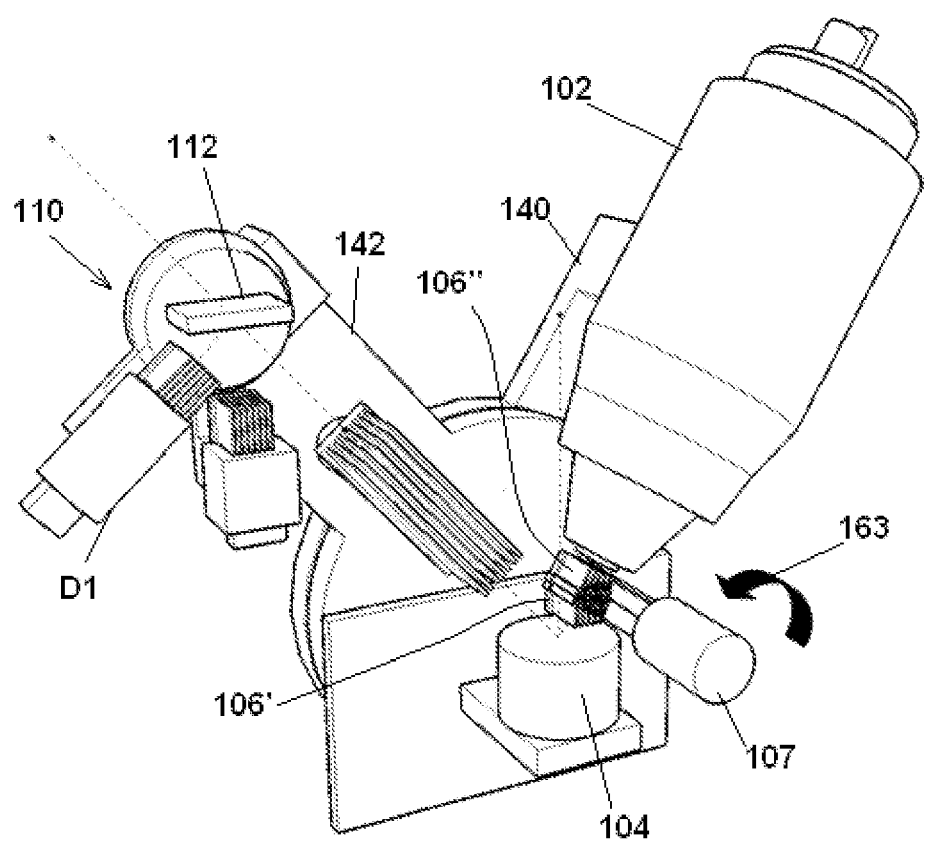
Figure 15A:
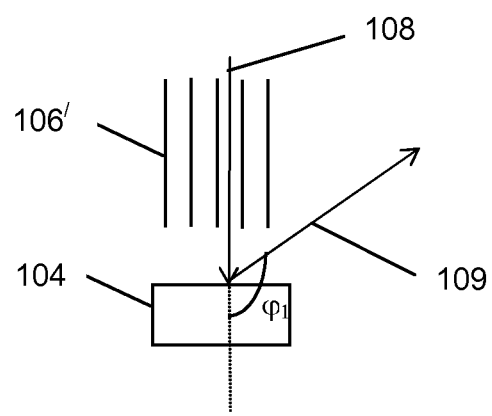
Figure 15B:
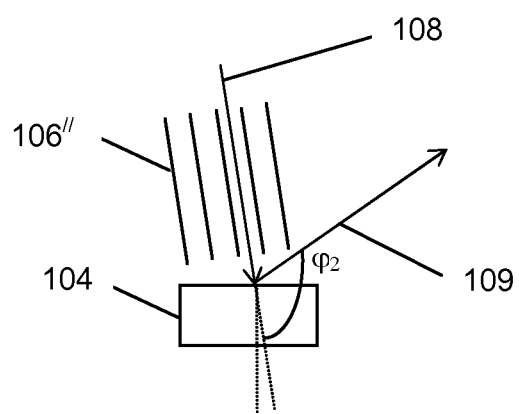

In a further embodiment, shown in FIG. 14, the diffraction angle, $\phi$, at the sample 104 is varied by tilting the primary collimator 106. As in previous embodiments, for XRD operation the combined XRD and XRF detection arrangement 110 is adjusted to a suitable diffraction angle $\theta$ at the crystal 112 so that X-rays of a characteristic wavelength of the X-ray tube 102 are sent to detector D1 (or alternatively D2) and the angle $\theta$ set in this way remains constant throughout the XRD analysis. In the FIG. 14 embodiment, the goniometer arms 140 and 142 are not moved during the XRD analysis and instead the diffraction angle, $\phi$, at the sample is varied only by tilting the primary collimator 106. For example, a first diffraction angle $\phi_1$ is set when the primary collimator 106 is in a first shown angular position 106'. The sample is irradiated with X-rays from the tube 102 whilst the primary collimator 106 is in the first position 106' and X-rays of the wavelength set by the detection arrangement 110 are diffracted by the sample and detected by the detector D1. The primary collimator 106 is then tilted by rotational movement of its arm 107 in direction 163 to a second shown angular position 106" thereby defining a second diffraction angle $\phi_2$. This is shown more clearly in the schematic drawings in FIG. 15A (first collimator position, 106') and FIG. 15B (second collimator position, 106"). The detection primary collimator 106 is then moved to appropriate corresponding third, fourth etc. angular positions to sequentially detect the intensity of diffracted X-rays of the fixed wavelength across the desired range of diffraction angle $\phi$. It will be appreciated that the range of angle $\phi$ which is accessible by moving only primary collimator 106 is quite limited compared to moving either of the goniometer arms 140 and 142 but it offers a low cost and simple option when only a small range of angle $\phi$ is required to be accessed, e.g. when scanning across only a single XRD peak such as free lime in cement samples is required. The detected X-ray intensities are processed etc. as described before by the computer (not shown), which also receives information on the angular position of primary collimator 106 for determination of diffraction angle $\phi$, in order to provide, e.g., an XRD pattern.

It will be appreciated that various hybrids of the embodiments shown in FIGS. 11 to 15 may be operated for XRD analysis, e.g. with a combination of any two or more of: (i) moving the X-ray tube 102, (ii) moving the detection arrangement 110, and (iii) tilting the primary collimator 106.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

Unless the context clearly indicates otherwise, as used herein the singular form of the terms herein are to be construed as including plural forms and vice versa.

Throughout the description and claims of this specification, the words "comprise", "including", "having" and "contain" and variations of the words, for example "comprising" and "comprises" etc, mean "including but not limited to", and are not intended to (and do not) exclude other components.

The use of any and all examples, or exemplary language (including "for instance", "such as", "for example", "e.g." and the like) provided herein, is intended merely to better illustrate the invention and does not indicate a limitation on the scope of the invention unless otherwise claimed.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The invention claimed is:

1. A method of performing X-ray diffraction (XRD) and/or X-ray fluorescence (XRF) analysis of a sample, comprising:
   irradiating a sample with X-rays from a polychromatic X-ray source;
   providing a combined XRD and XRF detection arrangement that is sequential x-ray detection channel comprising a scanning wavelength selector for sequentially scanning a wavelength range for XRF measurements and at least one X-ray detector for detecting X-rays selected by the scanning wavelength selector, wherein the X-ray source and the sequential x-ray detection channel are housed together with the sample inside a chamber that is capable of being evacuated and/or flushed with gas that is substantially spectrally transparent at the wavelength to be detected; and
   performing XRD analysis of the sample by selecting at least one fixed wavelength of X-rays diffracted by the sample using the scanning wavelength selector and detecting X-rays of the selected fixed wavelength(s) at one or more values of the diffraction angle φ at the sample using the X-ray detector(s); and/or
   performing XRF analysis of the sample by sequentially scanning wavelengths of X-rays emitted by the sample using the scanning wavelength selector and detecting X-rays of the scanned wavelengths using the X-ray detector(s).

2. A method as claimed in claim 1 further comprising providing a first collimating element between the X-ray source and the sample for irradiating the sample with parallel X-rays.

3. A method as claimed in claim 2 wherein performing the XRD analysis comprises varying the diffraction angle φ at the sample of the X-rays of the selected fixed wavelength(s) and detecting the X-rays of the selected fixed wavelength(s) at a plurality of values of the diffraction angle φ.

4. A method as claimed in claim 3 wherein the step of varying the diffraction angle φ at the sample of the selected fixed wavelength(s) of X-rays comprises one or more of the following:
   i) angularly moving the combined XRD and XRF detection arrangement about the sample;
   ii) angularly moving the X-ray source about the sample; and/or
   iii) tilting the first collimating element relative to the sample.

5. A method as claimed in claim 1 comprising tilting the sample.

6. A method as claimed in claim 1 comprising selecting one or more characteristic emission lines of the X-ray source as the fixed wavelengths in the XRD analysis by fixing a diffraction angle θ at a wavelength dispersive element of the wavelength selector.

7. A method as claimed in claim 1 comprising in the XRD analysis, selecting two or more fixed wavelengths and detecting the two or more fixed wavelengths of X-rays using two or more X-ray detectors.

8. A method as claimed in claim 1 comprising in the XRF analysis, scanning wavelengths of X-rays emitted by the sample by scanning a diffraction angle θ at a wavelength dispersive element of the wavelength selector while the diffraction angle φ at the sample is fixed.

9. An apparatus for performing X-ray diffraction (XRD) and X-ray fluorescence (XRF) analysis of a sample, comprising:
   a chamber that is capable of being evacuated and/or flushed with gas is substantially spectrally transparent at the wavelengths to be detected;
   a polychromatic X-ray source;
   a sample holder for holding a sample so that it may be irradiated by X-rays from the X-ray source; and
   a combined XRD and XRF detection arrangement that is sequential X-ray detection channel comprising a scanning wavelength selector for sequentially scanning a wavelength range for XRF measurements and at least one X-ray detector for detecting X-rays selected by the scanning wavelength selector;
   wherein the X-ray source, the sampler holder and the sequential X-ray detection channel are housed inside the chamber;
   wherein the apparatus is operable to perform:
   (i) XRD analysis of the sample by selecting at least one fixed wavelength of X-rays diffracted by the sample using the scanning wavelength selector and detecting X-rays of the selected wavelength(s) at one or more values of the diffraction angle φ at the sample using the X-ray detector(s); and
   (ii) XRF analysis of the sample by sequentially scanning wavelengths of X-rays emitted by the sample using the scanning wavelength selector and detecting X-rays of the scanned wavelengths using the X-ray detector(s).

10. An apparatus as claimed in claim 9 further comprising angular scanning means for varying the diffraction angle φ at the sample of the X-rays to be selected by the scanning wavelength selector.

11. An apparatus as claimed in claim 10 wherein one or both of the X-ray source and the combined XRD and XRF detection arrangement are mounted on a primary goniometer for varying the diffraction angle φ at the sample of the X-rays to be selected by the scanning wavelength selector.

12. An apparatus as claimed in claim 11 wherein the combined XRD and XRF detection arrangement further comprises at least one secondary goniometer for varying the angle θ of the X-rays at the scanning wavelength selector of the combined XRD and XRF detection arrangement.

13. An apparatus as claimed in claim 12 wherein the secondary goniometer(s) is mounted on the primary goniometer.

14. An apparatus as claimed in claim 9 wherein the apparatus further comprises a primary collimator to collimate X-rays from the source wherein the primary collimator is rotatably mounted for varying the diffraction angle φ at the sample of the X-rays to be selected by the scanning wavelength selector.

15. An apparatus as claimed in claim 9 further comprising a first collimating element between the X-ray source and the sample holder for irradiating the sample with a parallel X-ray beam.

16. An apparatus as claimed in claim 15 comprising one or more of the following means for varying the diffraction angle φ at the sample:

i) the combined XRD and XRF detection arrangement is angularly moveable about the sample;
ii) the X-ray source is angularly moveable about the sample; and/or
iii) the first collimating element is moveable relative to the sample.

17. An apparatus as claimed in claim 9 wherein the X-ray source is mounted at an angle of less than 90 degrees to the sample.

18. An apparatus as claimed in claim 9 wherein the sample holder is operable to tilt the sample.

19. An apparatus as claimed in claim 9 wherein the scanning wavelength selector comprises an entry collimating element, a wavelength dispersive element and at least one exit collimating element, the entry and exit collimating elements being positioned on either side of the wavelength dispersive element, the at least one X-ray detector being positioned after the at least one exit collimating element, and the entry and exit collimating elements being positioned at an angle $\theta$ to the wavelength dispersive element wherein the angle $\theta$ can be varied to select or scan wavelengths of X-rays.

20. An apparatus as claimed in claim 9 comprising using two or more X-ray detectors for detecting X-rays at two or more different wavelengths.

* * * * *